United States Patent [19]

Kadokura et al.

[11] Patent Number: 4,797,500

[45] Date of Patent: Jan. 10, 1989

[54] PURIFICATION OF ORGANOMETALLIC COMPOUNDS

[75] Inventors: Hidekimi Kadokura; Kenichi Sawara; Tadaaki Yako, all of Niihama, Japan

[73] Assignee: Sumitomo Chemical Company, Ltd., Osaka, Japan

[21] Appl. No.: 184,115

[22] Filed: Apr. 21, 1988

Related U.S. Application Data

[63] Continuation of Ser. No. 938,985, Dec. 3, 1986, abandoned.

[30] Foreign Application Priority Data

Dec. 3, 1985 [JP]  Japan ................. 60-272228

[51] Int. Cl.$^4$ ............................ C07F 5/00; C07F 5/06
[52] U.S. Cl. ................................. 556/1; 556/187
[58] Field of Search .............................. 556/187, 1

[56] References Cited

U.S. PATENT DOCUMENTS

| | | | |
|---|---|---|---|
| 1,938,179 | 12/1933 | Groll | 556/187 X |
| 2,691,668 | 10/1954 | Liegeer et al. | 556/187 |
| 2,744,127 | 5/1956 | Liegler et al. | 556/189 |
| 2,838,556 | 6/1958 | Cottle et al. | 556/187 X |
| 2,863,894 | 12/1958 | Smith | 556/187 X |
| 2,944,948 | 7/1960 | Giraitis | 556/187 X |
| 2,954,388 | 9/1960 | Nobis et al. | 556/187 |
| 3,006,942 | 10/1961 | Nobis | 556/187 X |

FOREIGN PATENT DOCUMENTS

| | | | |
|---|---|---|---|
| 148790 | 8/1984 | Japan | 556/187 U X |
| 4194 | 6/1985 | Japan | 556/187 U X |
| 980765 | 1/1965 | United Kingdom | 556/1 U X |
| 1462471 | 1/1977 | United Kingdom | 556/1 U X |

Primary Examiner—Paul F. Shaver
Attorney, Agent, or Firm—Wenderoth, Lind & Ponack

[57] ABSTRACT

A method for purifying an organometallic compound in which an organometallic compound of gallium, aluminum or indium is contacted with at least one metal selected from metallic sodium, metallic potassium and a sodium-potassium alloy. This method is especially efficacious when the high-purity organometallic compound is used as a semiconductor because, by the disclosed method, the silicon components are removed as impurities, which silicon material tends to lower the electrical characteristics of the semiconductor.

4 Claims, No Drawings

PURIFICATION OF ORGANOMETALLIC COMPOUNDS

This application is a continuation of now abandoned application Ser. No. 938,985, filed Dec. 3, 1986, now abandoned.

The present invention relates to a method for purifying an organometallic compound A high-purity organometallic compound is in use as a raw material in the electronic industry and as a raw material or a catalyst in the chemical industry, and in particular, in the electronic industry, it is used as a raw material for a compound semiconductor.

(PRIOR ART)

A general method for purifying an organometallic compound is a rectification method. For example, in Russian Journal of Physical Chemistry, 51(2), 301(1977) and in Zhurnal Prikladnoi Khimii, 48(8), 1810(1975), trimethylgallium was rectified with a glass or quartz packed column and a change in concentration of trace impurities was investigated before and after the rectification.

In Japanese Patent Publication No.4194/1985, a method was disclosed for removing transition metals in an organoaluminum compound by adsorption of them on silica gel.

Further, as a method of removing a small amount of organoaluminum contained in organogallium or organoindium, a method for treating the organometallic compound with alkalimetal fluoride such as potassium fluoride was mentioned in Journal of the American Chemical Society, 84(19), 3605(1962).

( Mooted points to be solved by the invention )

When an organometallic compound is used as a raw material for production of compound semiconductor, existence of silicon component as impurities results in a lowering in electric characteristics of the semiconductor, so that complete removal of silicon component from the organometallic compound is demanded.

However, it is difficult to remove a very small amount of silicon component completely by a rectification method as mentioned in Russian Journal of Physical Chemistry, 51(2), 301(1977). Other purification methods are less effective for removal of the silicon component.

( Means to solve mooted points )

The invention is a method for purifying an organometallic compound characterized in that an organometallic compound of gallium, aluminum, or indium is brought into contact with at least one metal selected from metallic sodium, metallic potassium, and a sodium-potassium alloy.

Organometallic compounds of gallium, aluminum, and indium to which the invention is applied may be ones having a hydrocarbon group or ones having both a hydrocarbon group and a halogen. However, the invention is very effective to organometallic compounds represented by a general formula $R_aMX_{3-a}$, where R represents an alkyl group of 1–4 carbon atoms, M represents gallium, aluminum, or indium, X represents a halogen atom, and a represents an integer of 2 or 3.

As the specific example of the above-mentioned organometallic compounds, there may be mentioned trialkyl metallic compounds $R_3M$ where R represents an alkyl of 1–4 carbon atoms and M is gallium, aluminum or indium, which includes such compounds as trimethylgallium, triethylgallium, tripropylgallium, tributylgallium, trimethylaluminum, triethylaluminum, tripropylaluminum, tributylaluminum, trimethylindium, triethylindium, tripropylindium, and tributylindium, and alkyl halide metallic compounds such as diethylgalliumchloride and dimethylaluminumchloride.

As a metal to be used for treatment of organometallic compound( abbreviated as a metal for treatment hereinafter) in the invention, metallic sodium, metallic potassium, a sodium-potassium alloy, and a mixture of at least two of these can all be used. However, a sodium-potassium alloy having a relatively low melting point and also having a composition region as a liquid even at a normal temperature is preferred.

The preferred composition region of sodium-potassium alloy for its good contact with an organometallic compound at a normal temperature is a region in which the alloy is liquid at a normal temperature, that is, a region having a content of 20–65 mol % of metallic sodium.

To produce the sodium-potassium alloy, metallic sodium and metallic potassium may be put into a container and be directly heated and melted, or they may be heated and melted in an appropriate inactive hydrocarbon solvent. To minimize a trouble that an organometallic compound is contaminated with impurities contained in metallic sodium and metallic potassium, it is preferred to use metallic sodium and metallic potassium of the highest-purity grade of commercially available those. It is preferred that the above-mentioned hydrocarbon solvent has a boiling point higher than the melting point of metallic sodium, and as the solvent, there may be mentioned saturated aliphatic hydrocarbons such as octane, nonane, decane, undecane, dodecane, paraffin oil, and the like and aromatic hydrocarbons such as toluene, xylene, and the like.

If an amount of a metal for treatment added is too much in the method of the invention, an organometallic compound is also consumed due to its reaction with the metal for treatment, so that a recovery ratio of organometallic compound is reduced. If the above-mentioned amount is too little, the metal for treatment is consumed due to its reaction with the organometallic compound, not enough contributing to removal of silicon component.

Therefore, a preferred amount of a metal for treatment added is the amount having a molar ratio of the sum of metallic sodium and metallic potassium to the organometallic compound of 0.05–0.6.

A time for purification of organometallic compound is 10 min or more, preferably 30 min–3 hours in an inert gas atmosphere such as nitrogen, argon, or the like and a temperature for purification of the same is not specially limitative so far as an organometallic compound and a metal for treatment are both maintained liquid but it is best to bring the both into contact with each other within a range of normal temperature to 120° C.

The contacting method may be any publicly-known, common method as far as liquid-liquid contact and mixing are carried out. However, it is usual to adopt a method to add a metal for treatment while an organometallic compound is stirred in a container with a stirrer or a method to add an organometallic compound to a metal for treatment in the same container as the above. In this process, to improve a contact efficiency of the both, it is preferred to carry out strong stirring and to add an organometallic compound or a metal for treatment slowly.

An organometallic compound and a metal for treatment can be diluted in an inactive hydrocarbon solvent to carry out the contact of the both. As such an inactive hydrocarbon solvent, a saturated aliphatic hydrocarbon such as hexane, heptane, octane, nonane, decane, undecane, dodecane, paraffin oil, or the like, an alicyclic hydrocarbon such as cyclohexane, cycloheptane, or the like, or an aromatic hydrocarbon such as toluene, xylene, or the like is used. Above all, an inactive hydrocarbon solvent having a boiling point higher than the boiling point of organometallic compound and the melting-point of metal for treatment is preferred. An organometallic compound after being purification-treated is distilled to separate it from a metal for treatment containing impurities and thus a purified organometallic compound is recovered. If a solvent is used, distillation is needed at least once more to separate a purified organometallic compound from the solvent.

The method of the invention can be carried out by any one of batchwise process and continuous process.

Further, the silicon component mentioned in the invention means an inorganic silicon compound such as metallic silicon or silica, or an organic silicon compound such as alkyl silane or alkyl halide silane.

It is considered that the silicon component is derived from silicon components contained in raw materials used for production of organometallic compound, in the material of apparatus or utensils used for the production, or in dust suspending in the atmosphere.

The silicon component existent in an organometallic compound has various bad effects on the above-mentioned use of organometallic compound.

For example, if the organometallic compound containing a silicon component is used as a raw material for production of compound semiconductor, as a bad effect the silicon component has on the compound semiconductor, there may be mentioned that electron mobility of the resulting semiconductor is reduced, thereby lowering the electric performance of semiconductor, and when a thin film of semiconductor is grown, it is hard to control in an electronic level.

(EFFECT OF INVENTION)

A content of silicon component in an organometallic compound to which the invention is applied is not specially limited. However, the invention is, in particular, effective to an organometallic compolund containing about 10 ppm or less of silicon component, and such an organometallic compound is suitable for production of purified organometallic compound having a content of 0.5 ppm or less of silicon component and which is considered containing substantially no silicon component. The thus purified organometallic compound can be used without any trouble as a raw material for the electronic industry.

(EXAMPLE)

A content of silicon component shown in examples was determined by hydrolyzing an organometallic compound before dissolving the hydrolysis product in diluted hydrochloric acid and then analyzing the resulting solution by an atomic absorption spectrometry.

EXAMPLE 1

After an air in an apparatus consisting of a 500 cc glass flask with a stirrer and a reflux condenser was replaced with nitrogen, 100 ml of n-dodecane, 0.2 mol of metallic sodium, and 0.8 mol of metallic potassium were put into the flask and then metallic sodium and metallic potassium were heated and melted under slow stirring to prepare a sodium-potassium alloy.

Next, 2 mols of trimethylgallium containing 7 ppm of silicon component were added slowly to the entire amount of the dispersion of sodium-potassium alloy in n-dodecane in the flask at a room temperature, and the mixture was heated under stirring at the boiling point of trimethylgallium for 1 hour. After that, trimethylgallium was distilled off by normal pressure distillation to separate it from the alloy and the solvent. A concentration of silicon component in the resulting trimethyl gallium was 0.1 ppm.

EXAMPLE 2

The apparatus of Example 1 was used, and by a similar process, a dispersion of sodium-potassium alloy in n-dodecane consisting of 0.05 mol of metallic sodium, 0.15 mol of metallic potassium and 100 ml of n-dodecane was prepared. Subsequently, 2 mols of trimethylaluminum containing 5 ppm of silicon component were added to the dispersion and the mixture was heated for 1 hour under stirring. After that, purified trimethylaluminum was recovered by vacuum distillation at pressure of 100 mm Hg, and a concentration of silicon component in the trimethylaluminum was 0.3 ppm.

EXAMPLE 3

The same apparatus as in Example 1 was used and by a similar method, a dispersion of sodium-potassium alloy in a paraffin oil consisting of 0.25 mol of metallic sodium, 0.25 mol of metallic potassium, and 100 ml of paraffin oil was prepared. Subsequently, 2 mols of triethylindium containing 10 ppm of silicon component were added to the dispersion and the mixture was heated at 80° C. for 2 hours under stirring.

After that, purified triethylindium was recovered by vacuum distillation at pressure of 20 mm Hg, and a concentration of silicon component in the triethylindium was 0.2 ppm.

What is claimed is:

1. A method for purifying a trialkylmetallic compound of the formula $R_3M$ wherein R represents an alkyl group of 1-4 carbon atoms and M represents gallium, aluminum or indium, which comprises contacting said trialkylmetallic compound with at least one metallic sodium, metallic potassium or metallic potassium alloy at a temperature and a time sufficient to remove impurities, including silicon impurities, from the trialkylmetallic compound, wherein the molar ratio of the total of sodium and potassium to the trialkylmetallic compound is 0.05 to 0.6.

2. A method according to claim 1 in which the temperature of contact ranges from normal temperature to 120° C. and the time of contact is from 30 minutes to 3 hours.

3. A method according to claim 2 in which the contact is carried out in the presence of an inactive hydrocarbon solvent having a boiling point higher than that of the trialkylmetallic compound.

4. A method for purifying an trialkylmetallic compound as set forth in claim 1 wherein a content of sodium in a sodium-potassium alloy is 20-65 mol percent.

* * * * *